(12) United States Patent
Li et al.

(10) Patent No.: US 11,585,777 B2
(45) Date of Patent: Feb. 21, 2023

(54) METHOD AND DEVICE FOR DETECTING A COMPONENT IN A SAMPLE

(71) Applicants: InnoTech Alberta Inc., Edmonton (CA); The Governors of the University of Alberta, Edmonton (CA)

(72) Inventors: Xiujie Li, Edmonton (CA); Jie Chen, Edmonton (CA); Jian Yang, Edmonton (CA); Scott Mackay, Edmonton (CA); Lian C. T. Shoute, Edmonton (CA)

(73) Assignees: InnoTech Alberta Inc., Edmonton (CA); The Governors of the University of Alberta, Edmonton (CA)

( * ) Notice: Subject to any disclaimer, the term of this patent is extended or adjusted under 35 U.S.C. 154(b) by 215 days.

(21) Appl. No.: 16/395,062

(22) Filed: Apr. 25, 2019

(65) Prior Publication Data
US 2019/0331633 A1    Oct. 31, 2019

Related U.S. Application Data

(60) Provisional application No. 62/663,959, filed on Apr. 27, 2018.

(51) Int. Cl.
*G01N 27/327*    (2006.01)
*C12Q 1/04*    (2006.01)

(52) U.S. Cl.
CPC .......... *G01N 27/3276* (2013.01); *C12Q 1/04* (2013.01)

(58) Field of Classification Search
CPC .............................. G01N 27/3276; C12Q 1/04
See application file for complete search history.

(56) References Cited

U.S. PATENT DOCUMENTS

| 4,837,146 A | 6/1989 | Morrall et al. |
| 5,187,064 A | 2/1993 | Petersen et al. |

(Continued)

FOREIGN PATENT DOCUMENTS

| BR | PI0805316 A2 | 8/2010 |
| BR | 102015024029 A2 | 3/2017 |

(Continued)

OTHER PUBLICATIONS

Mendes, R. K., et al. "Development of an electrochemical immunosensor for Phakopsora pachyrhizi detection in the early diagnosis of soybean rust." Journal of the Brazilian Chemical Society 20.4 (2009): 795-801. (Year: 2009).*

(Continued)

*Primary Examiner* — Robert J Eom
(74) *Attorney, Agent, or Firm* — Borden Ladner Gervais LLP; Michael Damiani

(57) ABSTRACT

The present disclosure provides a biosensor for detecting the presence of and/or the amount of at least one fungal plant pathogen in a sample, comprising: a support structure; at least two interdigitated electrodes coupled to the support structure, wherein at least one of the interdigitated electrodes is functionalized with a linker coupled to at least one biological component that recognizes the at least one fungal plant pathogen; and an impedance measurement circuit coupled to the at least two interdigitated electrodes. The present disclosure also provides methods of detecting the presence of and/or the amount of at least one fungal plant pathogen in a sample, methods of making the biosensor described herein, as well as methods and uses of using the herein described biosensor for detecting the presence of and/or amount of at least one fungal plant pathogen.

7 Claims, 7 Drawing Sheets

(56) References Cited

U.S. PATENT DOCUMENTS

| | | |
|---|---|---|
| 6,835,552 B2 | 12/2004 | Miles et al. |
| 7,910,702 B2 | 3/2011 | Kav et al. |
| 8,399,262 B2 | 3/2013 | Mazzari et al. |
| 8,932,868 B2 | 1/2015 | Van et al. |
| 2003/0104390 A1 | 6/2003 | Etienne et al. |
| 2005/0059105 A1 | 3/2005 | Alocilja et al. |
| 2010/0075340 A1 | 3/2010 | Javanmard et al. |
| 2013/0319880 A1 | 12/2013 | Wu et al. |
| 2013/0334042 A1 | 12/2013 | Grieve et al. |

FOREIGN PATENT DOCUMENTS

| | | |
|---|---|---|
| ES | 2307430 B1 | 10/2009 |
| KR | 20090085913 A | 8/2009 |
| TW | I486584 B | 6/2015 |
| WO | 2017123697 A1 | 7/2017 |

OTHER PUBLICATIONS

Zou, Zhiwei, Soohyun Lee, and Chong H. Ahn. "A polymer microfluidic chip with interdigitated electrodes arrays for simultaneous dielectrophoretic manipulation and impedimetric detection of microparticles." IEEE Sensors journal 8.5 (2008): 527-535. (Year: 2008).*

Wang, Zhan, et al. "Electrocatalytic oxidation of phytohormone salicylic acid at copper nanoparticles-modified gold electrode and its detection in oilseed rape infected with fungal pathogen Sclerotinia sclerotiorum." Taianta 80.3 (2010): 1277-1281. (Year: 2010).*

Khater, Mohga, Alfredo de la Escosura-Muñiz, and Arben Merkçi. "Biosensors for plant pathogen detection." Biosensors and Bioelectronics 93 (2017): 72-86. (Year: 2017).*

Ho, Ja-an Annie, et al. "Ultrasensitive electrochemical detection of biotin using electrically addressable site-oriented antibody immobilization approach via aminophenyl boronic acid." Biosensors and Bioelectronics 26.3 (2010): 1021-1027. (Year: 2010).*

Li, Susie, et al. "Building an antibody-based pathogen specific plant disease monitoring device for agriculture pest management." 2014 IEEE Biomedical Circuits and Systems Conference (BioCAS) Proceedings. IEEE, 2014. (Year: 2014).*

Abad et al., "Immobilization of Peroxidase Glycoprotein on Gold Electrodes Modified with Mixed Epoxy-Boronic Acid Monolayers," Journal of American Chemical Society, Oct. 2002, vol. 124(43), pp. 12845-12853.

Adak et al., "Fabrication of Antibody Microarrays by Light-Induced Covalent and Oriented Immobilization," ACS Applied Materials and Interfaces, Jun. 2014, vol. 6(13), pp. 10452-10460.

Almquist et al., "Monitoring of Plant and Airborne Inoculum of Sclerotinia Sclerotiorum in Spring Oilseed Rape Using Real-Time PCR," Plant Pathology, Feb. 2015, vol. 64(1), pp. 109-118.

Aveskamp et al., "Biology and Recent Developments in the Systematics of Phoma, A Complex Genus of Major Quarantine Significance," Fungal Diversity, 2008, vol. 31, pp. 1-18.

Badawy et al., "Differential Reactions Between the Genus Brassica and Aggressive Single Spore Isolates of Leptosphaeria Maculans," Journal of Phytopathology, Feb. 1991, vol. 131 (2), pp. 109-119.

Batalla et al., "Immobilization of Antibodies Through the Surface Regions Having the Highest Density in Lysine Groups on Finally Inert Support Surfaces," Process Biochemistry, Mar. 2009, vol. 44(3), pp. 365-368.

Berggren et al., "Capacitive Biosensors," Electroanalysis, Mar. 2001, vol. 13(3), pp. 173-180.

Bom and Boland et al., "Evaluation of Disease Forecasting Variables for Sclerotinia Stem Rot (Sclerotinia Sclerotiorum) of Canola," Canadian Journal of Plant Science, Apr. 2000, vol. 80(4), pp. 889-898.

Bonnani and Del Valle., "Use of Nanomaterials for Impedimetric DNA Sensors: A Review," Analytica Chimica Acta, Aug. 2010, vol. 678(1), pp. 7-17.

Canola Council of Canada, Annual Report 2017. https://www.canolacouncil.org/media/595577/ccc_ar201 7_50_yrs_firsts.pdf.

Clarkson et al., "Forecasting Sclerotinia Disease on Lettuce: A Predictive Model for Carpogenic Germination of Sclerotinia Sclerotiorum Sclerotia," Phytopathology, May 2007, vol. 67 (5), pp. 621-631.

Clarkson et al., "Forecasting Sclerotinia Disease on Lettuce: Toward Developing a Prediction Model for Carpogenic Germination of Sclerotia," Phytopathology, Mar. 2004, vol. 94(3), pp. 268-279.

Couniot et al., "Lytic Enzymes as Selectivity Means for Label-Free, Microfluidic and Impedimetric Detection of Whole-Cell Bacteria Using ALD-A12O3 Passivated Microelectrodes," Biosensors and Bioelectronics, May 2015, vol. 67, pp. 154-161.

Daniels and Pourmand., "Label-Free Impedance Biosensors: Opportunities and Challenges," Electroanalysis, May 2007, vol. 19(12), pp. 1239-1257.

Del Rio et al., "Impact of Sclerotinia Stem Rot On Yield of Canola," Plant Disease, Feb. 2007, vol. 91 (2), pp. 191-194.

Doiron et al., "Endothelial Nanoparticle Binding Kinetics are Matrix and Size Dependent," Biotechnology and Bioengineering, Dec. 2011, vol. 108 (12), pp. 2988-2998.

Duval et al., "Key Steps Towards the Oriented Immobilization of Antibodies Using Boronic Acids," Analyst, Aug. 2015, vol. 140(19), pp. 6467-6472.

Gobel et al., "Production of Polyclonal and Monoclonal Antibodies Against Hyphae from Arbuscular Mycorrhizal Fungi," Critical Reviews in Biotechnology, 1995, vol. 15 (3-4), pp. 293-304.

Guan et al., "Impedimetric Biosensors," Journal of Bioscience and Bioengineering, 2004, vol. 97(4), pp. 219-226.

Guimera et al., "Effect of Surface Conductivity on the Sensitivity of Interdigitated Impedimetric Sensors and Their Design Considerations," Sensors and Actuators B: Chemical, Feb. 2015, vol. 207, pp. 1010-1018.

Ho et al., "Ultrasensitive Electrochemical Detection of Biotin Using Electrically Addressable Site-Oriented Antibody Immobilization Approach via Aminophenyl Boronic Acid," Biosensors and Bioelectronics, Nov. 2010, vol. 26(3), pp. 1021-1027.

Jamaux et al., "Early Stages of Infection of Rapeseed Petals and Leaves by Sclerotinia Sclerotiorum Revealed by Scanning Electron Microscopy," Plant Pathology, 1996, vol. 44(1), pp. 22-30.

Javanmard et al., "Electrical Detection of Protein Biomarkers Using Bioactivated Microfluidic Channels," Lab on a chip. May 2009, vol. 9(10), pp. 1429-1434.

Jones et al., "A Polymerase Chain Reaction Assay for Ascosporic Inoculum of Sclerotinia Species," New Zealand Journal of Crop and Horticultural Science, Feb. 2015, vol. 43(3), pp. 233-240.

Kennedy and Wakeham., "New Methods for Detecting and Enumerating Fungal Spores of Plant Pathogens," Plant Protection Science, 2002, vol. 38 (Special Issue 1), pp. 38-42.

Koch et al., "A Crop Loss-Related Forecasting Model for Sclerotinia Stem Rot in Winter Oilseed Rape," Phytopathology, Apr. 2007, vol. 97(9), pp. 1186-1194.

Kohn., "Delimitation of the Economically Important Plant Pathogenic Sclerotinia Species," Phytopathology, Jan. 1979, vol. 69(8), pp. 881-886.

Kutcher et al., "Low-Drift Fungicide Application Technology for Sclerotinia Stem Rot Control in Canola," Crop Protection, Sep. 2006, vol. 25, pp. 640-646.

Lavilla et al., "Production of Polyclonal Antibodies Against Spores of Clostridium Tyrobutyricum, A Contaminant Affecting the Quality of Cheese: Characterisation of the Immunodominant Protein," Food and Agricultural Immunology, Mar. 2008, vol. 19(1), pp. 77-91.

Li et al., "Canola May Soon Be Able to Text You when It Needs to Be Sprayed: Nano-Biosensor is More Accurate than Checklists Determining When to Spray for Sclerotinia," Alberta Farm Express, Jan. 2017, pp. 18.

Link and Johnson., White Mold (Sclerotinia), 2007. http://www.apsnet.org/edcenter/intropp/lessons/fungi/ascomycetes/Pages/WhiteMold.aspx.

Lisdat et al., "The Use of Electrochemical Impedance Spectroscopy for Biosensing," Analytical and Bioanalytical Chemistry, Feb. 2008, vol. 391(5), pp. 1555-1567.

(56) References Cited

OTHER PUBLICATIONS

Liu et al., "A General Signal Amplification Strategy for Non-Faradaic Impedimetric Sensing: Trastuzumab Detection Employing a Peptide Immunosensor," Analytical Chemistry, Mar. 2017, vol. 89(7), pp. 4013-4020.
Luo and Davis., "Electrical Biosensors and the Label Free Detection of Protein Disease Biomarkers," Chemical Society Reviews, Apr. 2013, vol. 42(13), pp. 5944-5962.
Mackay et al., "Simulations of Interdigitated Electrode Interactions with Gold Nanoparticles for Impedance-Based Biosensing Applications," Sensors, Sep. 2015, vol. 5(9), pp. 22192-22208.
Makaraviciute and Ramanaviciene., "Site-Directed Antibody Immobilization Techniques for Immunosensors," Biosensors and Bioelectronics, Jun. 2013, vol. 50, pp. 460-471.
McLaren et al., "Predicting Diseases Caused by Sclerotinia Sclerotiorum on Canola and Bean—A Western Canadian Perspective," Canadian Journal of Plant Pathology, Sep. 2004, vol. 26(4), pp. 489-497.
Mirsky et al., "Capacitive Monitoring of Protein Immobilization and Antigen-antibody Reactions on Monomolecular Alkylthiol Films on Gold Electrodes," Biosensors and Bioelectronics, Apr. 1997, vol. 12(9-10), pp. 977-989.
Parker et al., "Evaluation of Air Sampling and Detection Methods to Quantify Airborne Ascospores of Sclerotinia Sclerotiorum," Plant Disease, Jan. 2014, vol. 98(1), pp. 32-42.
Prodromidis., "Impedimetric Immunosensors—A Review," Electrochimica Acta, May 2010, vol. 55(14), pp. 4227-4233.
Pudry., "Sclerotinia Sclerotiorum: History, Diseases and Symptomatology, Host Range, Geographic Distribution, and Impact," Phytopathology, 1979, vol. 69(8), pp. 875-880.
Randviir et al., "Electrochemical Impedance Spectroscopy: An Overview of Bioanalytical Applications," Analytical Methods, 2013, vol. 5(5), pp. 1098.
Rickert et al., "A Mixed Self-Assembled Monolayer for An Impedimetric Immunosensor," Biosensors and Bioelectrons, 1996, vol. 11(8), pp. 757-768.
Rusmini et al., "Protein Immobilization Strategies for Protein Biochips," Biomacromolecules, Feb. 2007, vol. 8(6), pp. 1775-1789.
Schmechel and Lewis., "The Production of Species-Specific Monoclonal Antibodies (Mabs) Against the Allergenic and Toxigenic Fungus Stachybotrys Chartarum," The FASEB Journal, Jan. 2001, vol. 15(4), pp. A662, Abstract # 523.1.
Shapira et al., "Development of Polyclonal Antibodies for Detection of Aflatoxigenic Molds Involving Culture Filtrate and Chimeric Proteins Expressed in *Escherichia coli*," Applied and Environmental Microbiology, Mar. 1997, vol. 63 (3), pp. 990-995.
Shoute et al., "Immuno-impedimetric Biosensor for Onsite Monitoring of Ascospores and Forecasting of Sclerotinia Stem Rot of Canola," Scientific Reports, Aug. 2018, vol. 8(1), pp. 12396.
Soledade et al., "HPLC Analyses of Cultures of Phoma Spp.: Differentiation Among Groups and Species Through Secondary Metabolite Profiles," Canadian Journal of Microbiology, 2000, vol. 46(8), pp. 685-691.
Stace-Smith et al., "Monoclonal Antibodies Differentiate the Weakly Virulent From the Highly Virulent Strain of Leptosphaeria Maculans, The Organism Causing Blackleg of Canola," Canadian Journal of Plant Pathology, Apr. 1993, vol. 15(3), pp. 127-222.
Trilling et al., "The Effect of Uniform Capture Molecule Orientation on Biosensor Sensitivity: Dependence on Analyte Properties," Biosensors and Bioelectronics, Feb. 2013, vol. 40(1), pp. 219-226.
Tsouti et al., "Capacitive Microsystems for Biological Sensing," Biosensors & Bioelectronics, Sep. 2011, vol. 27(1), pp. 1-11.
Turkington et al., "Managing Sclerotinia in Oilseed and Pulse Crops," Insects and Diseases, 2011, vol. 4, pp. 105-113.
Vaisocherova et al., "Functionalizable Low-Fouling Coatings for Label-Free Biosensing in Complex Biological Media: Advances and Applications," Feb. 2015, vol. 407(14), pp. 3927-3953.
Wang et al., "Isolation and Identification of Sclerotinia Stem Rot Causal Pathogen in *Arabidopsis thaliana*," Journal of Zhejiang University Science B, Aug. 2008, vol. 9(10), pp. 818-822.
Willetts and Wong., "The Biology of Sclerotinia Sclerotiorum, S.Trifoliorum, and S.Minor With Emphasis on Specific Nomenclature," The Botanical Review, Apr. 1980, vol. 46(2), pp. 101-165.
Xing et al., "Dynamic Monitoring of Cytotoxicity on Microelectronic Sensors," Chemical Research in Toxicology, Feb. 2005, vol. 18(2), pp. 154-161.
Ziesman et al., "A Quantitative PCR System for Measuring Sclerotinia Sclerotiorum in Canola (*Brassica napus*)," Plant Disease, May 2016, vol. 100(5), pp. 984-990.

* cited by examiner

———— 100 μm

METHOD AND DEVICE FOR DETECTING A COMPONENT IN A SAMPLE

FIELD

The present disclosure relates to a method and immuno-impedimetric biosensor for detecting a plant pathogen in a sample.

BACKGROUND

The following paragraphs are not an admission that anything discussed in them is prior art or part of the knowledge of persons skilled in the art.

Plant diseases have significant impacts on crop quality and yield and have caused famine and economic losses. Over eighty percent of plant diseases are caused by fungi. Fungi are the number one cause of crop loss worldwide. The most well-known plant diseases caused by fungal pathogens are *fusarium* head blight of wheat and barley, black stem rust and leaf rust of wheat, *sclerotinia* stem rot and blackleg of canola, leaf blight of corn, ergot of sorghum, late blight of potato, *fusarium* wilts of cotton and flax, powdery and downy mildews of grape etc. Fungi spread from one plant to another and from one location to another in several ways. Most pathogens produce spores, either through asexual or sexual reproduction, that aid in the dissemination of the fungi. These spores may be moved by wind, insects, or water. Plant fungal pathogens cause tissue decay and eventual death of the plant. In addition to destroying plant tissue directly, some plant pathogens spoil crops by producing potent toxins.

The primary tool used to control fungal disease spread is the application of fungicides [1]. In order to be effective, foliar fungicides need to be applied during the key stage of infection, that is, early flowering and before the appearance of symptoms in the crops. Systematic application of fungicides may be unprofitable because the outbreak of plant disease can vary greatly among fields and years.

A number of forecasting systems have been developed to predict the risk of fungal plant disease. The methodology adopted for risk assessment includes recording the amount of continuous rainfall for a number of days, soil moisture and apothecium development, temperature, crop canopy development, crop rotation, and crop disease levels in the previous years. Additional tools such as testing petals for infection caused by *S. sclerotiorum* ascospores and weather-based forecasting maps have been adopted in Canada [2, 3]. However, these approaches for risk assessment may be time consuming, labor intensive as they require constant field testing, and/or may not predict the risk in a timely manner.

INTRODUCTION

The following introduction is intended to introduce the reader to this specification but not to define any invention. One or more inventions may reside in a combination or sub-combination of the instrument elements or method steps described below or in other parts of this document. The inventors do not waive or disclaim their rights to any invention or inventions disclosed in this specification merely by not describing such other invention or inventions in the claims.

Airborne ascospores, conidiospores, aeciospores, and urediniospores are the dominant source of the spread of infection in crop plants. Methods and devices that can directly detect airborne ascospores and/or conidiospores may provide a more efficient measurement of the risk of crop infection. Quantitative real-time polymerase chain reaction (qPCR) has been developed as the method of choice for monitoring airborne ascospores by amplifying a selected segment of their DNA for detection and quantification [4, 5, 6, 7]. Although qPCR has the sensitivity and selectivity to detect the presence of pathogens to a level as low as a single spore in the sample, it has a number of disadvantages in terms of cost and complexity of the method due to the simultaneous requirements of thermal cycling and fluorescence detection which may render the technique unsuitable for routine onsite field applications.

There remains a need for methods and devices for detecting fungal plant pathogens that are less costly, physically miniaturized, and/or more capable of onsite field application, in comparison to one or more known methods and devices for detecting fungal plant pathogens.

The present disclosure provides a biosensor for detecting the presence of and/or the amount of at least one fungal plant pathogen in a sample, comprising at least a first electrical conductor that detects the at least one fungal plant pathogen in the sample, and at least a second electrical conductor coupled to the at least first electrical conductor to measure the impedance therebetween and correlate changes in impedance to the presence of and/or amount of the at least one fungal plant pathogen in the sample.

The present disclosure also discusses methods of detecting the presence of and/or the amount of at least one fungal plant pathogen in a sample, methods of making the biosensor described herein, as well as methods and uses of using the herein described biosensor for detecting the presence of and/or amount of at least one fungal plant pathogen.

The present disclosure provides a biosensor for detecting the presence of and/or the amount of at least one fungal plant pathogen in a sample, comprising: a support structure; at least two interdigitated electrodes coupled to the support structure, wherein at least one of the interdigitated electrodes is functionalized with a linker coupled to at least one biological component that recognizes the at least one fungal plant pathogen; and an impedance measurement circuit coupled to the at least two interdigitated electrodes.

The at least one fungal plant pathogen may infect a canola plant, a wheat plant, a barley plant, a corn plant, a rice plant, a millet plant, a sorghum plant, or a combination thereof. The at least one fungal plant pathogen may be *Sclerotinia sclerotiorum, Fusanium graminearum, F. avenaceum, F. poae, F. sporotrichioedes, Puccinia graminis, Puccinia triticina, P. recondite, P. striiformis, Erysiphe graminis* f.sp. *Tritici, Glomerella graminicola* (anamorph *Colletotrichum graminicola*), *Pyrenophora tritici-repentis* (telomorph) and *Drechslera tritici-repentis, Pyrenophora trichostoma, Urocystis agropyri, Sclerotinia borealis, Septoria* spp., *Stagnospora* spp., *Pyrenophora teres* tares, *Pyrenophora teres maculate, Claviceps purpurea, Alternaria* spp., *Heminthosporium* spp, *Psudocercosporella herpotrichoides, Glomerella graminicola* (anamorphic), *Colletotrichum graminicola, Fusarium verticillioides, Gibberella zeae, Aspergillus flavus, A. parasiticus, Lasiodiplodia theobromae, Physoderma maydis, Exserohilum turcicum, Cochliobolus heterostrophu, Cercospora zeae-maydis* and *Cercospora zeinaor, Cochliobolus carbonum, Stenocarpella maydis, Puccinia polysora, Magnaporthe oryzae, Cochliobolus miyabeanus, Ascochyta oryzae, Drechslera gigantean, Microdochium albescens, Cercospora oryzae, Puccinia graminis* f.sp. *oryzae, Uromyces coronatus, Ramularia oryzae, Bipolaris setariae, Cercospora penniseti, Curvularia penniseti, Dactuliophora elongata, Drechslera dematioidea, Claviceps*

*fusiformis, Exserohilum rostratum, Beniowskia sphaeroidea, Myrothecium roridum, Phyllosticta penicillariae, Pyricularia grisea, Puccinia substriata, Moesziomyces penicillariae, Sclerotium rolfsii, Fusarium moniliforme, Gleocercospora sorghi, Sarocladium strictum* (syns *Acremonium strictum*), *Cephalosporium acremonium, Macrophomina phaseolina, Claviceps africana, Sphacelia sorghi, Fusarium* spp., *Fusarium moniliforme* (syn. *Gibberella fujikuroi*), *F. thapsinum* (syn. *G. thapsina*), *Aspergillus* spp., *Fusarium andiyazi, F. nygamai, Penicillium* spp., *Cercospora sorghi, Passalora fusimaculans* (syn. *Cercospora fusimaculans*), *Setosphaeria turcica* (syns. *Exserohilum turcicum, Helminthosporium turcicum*), *Periconia circinata, Ramulispora sorghicola, Gibberella fujikuroi* (syns. *Fusarium moniliforme* var. *subglutinans G. fujikuroi* var. *subglutinans, G. intermedia, F. proliferatum*), *Ascochyta sorghi, Puccinia purpurea, Sclerotium rolfsii* (syn. *Athelia rolfsii*), *Ramulispora sorghi, Phyllachora sacchari, Bipolaris sorghicola* (syns. *B. cookei, Helminthosporium cookei.*), *Gloeocercospora sorghi*, or a combination thereof. The at least one fungal plant pathogen may be *Sclerotinia sclerotiorum*. The at least one fungal plant pathogen may be the apothecia of the at least one fungal plant pathogen. The apothecia may be at least one airborne ascospore or conidiospore released from the apothecia.

The linker may be a SAM, a macromolecule, or a thin layer of polymer. The linker may be a SAM that comprises a thiol head group and optionally, a boron functional group.

The biological component may be an antibody or fragment thereof.

The at least two interdigitated electrodes may comprise a gold surface. The fingers of a pair of interdigitated electrodes, together, may have an about square shape. The square shape may have a length of about 3 mm, a width of about 3 mm, a thickness of about 110 nm, and the gap between the fingers may be about 3 μm.

The impedance measurement circuit may comprise a potentiostat.

The support structure may be a silicon wafer.

The biosensor may be a non-faradaic biosensor.

The present disclosure also provides a method of making a biosensor for detecting the presence of and/or the amount of at least one fungal plant pathogen in a sample, comprising: contacting an interdigitated electrode with an aqueous solution comprising a linker, the interdigitated electrode being in electrical communication with at least a second interdigitated electrode; contacting the interdigitated electrode with an aqueous solution comprising EDC and NHS; contacting the interdigitated electrode with an aqueous solution comprising APBA; and contacting the interdigitated electrode with a solution comprising at least one biological component that recognizes the at least one fungal plant pathogen. The method may further comprise the step of: applying a PDMS mask to the interdigitated electrode. The linker may be is a SAM, a macromolecule, a thin layer of polymer, or 6-MHA and 11-MUA. The linker may be a SAM that comprises a thiol head group and optionally, a boron functional group.

The present disclosure also provides a method of detecting the presence of and/or the amount of at least one fungal plant pathogen in a sample, comprising: measuring the impedance of a biosensor coupled to at least one biological component that recognizes the at least one fungal plant pathogen; contacting the sample with the biosensor; measuring the impedance of the biosensor in contact with the sample; and correlating the change of impedance with the presence and/or the amount of the at least one fungal plant pathogen in the sample. The biological component may be an antibody or fragment thereof.

The present disclosure also provides a method of detecting the presence of and/or the amount of at least one fungal plant pathogen in a sample, comprising: measuring the impedance of a herein described biosensor; contacting the sample with the biosensor; measuring the impedance of the biosensor in contact with the sample; and correlating the change of impedance with the presence and/or the amount of the at least one fungal plant pathogen in the sample.

The correlating step may comprise correlating the change of impedance with a standard curve of known impedances of known amounts of the at least one fungal plant pathogen.

The impedances may be measured by applying about 10 mV sinusoidal excitation perturbation at 0 V DC in a frequency range from about 10 Hz to about 1 MHz.

The at least one fungal plant pathogen may infect a canola plant, a wheat plant, a barley plant, a corn plant, a rice plant, a millet plant, a sorghum plant, or a combination thereof. The at least one fungal plant pathogen may be *Sclerotinia sclerotiorum, Fusarium graminearum, F. avenaceum, F. poae, F. sporotrichioedes, Puccinia graminis, Puccinia triticina, P. recondite, P. striiformis, Erysiphe graminis* f.sp. *Tritici, Glomerella graminicola* (anamorph *Colletotrichum graminicola*), *Pyrenophora tritici-repentis* (telomorph) and *Drechslera tritici-repentis, Pyrenophora trichostoma, Urocystis agropyri, Sclerotinia borealis, Septoria* spp., *Stagnospora* spp., *Pyrenophora teres* tares, *Pyrenophora teres maculate, Claviceps purpurea, Alternaria* spp., *Hemintshosporium* spp, *Psudocercosporella herpotrichoides, Glomerella graminicola* (anamorphic), *Colletotrichum graminicola, Fusarium verticillioides, Gibberella zeae, Aspergillus flavus, A. parasiticus, Lasiodiplodia theobromae, Physoderma maydis, Exserohilum turcicum, Cochliobolus heterostrophu, Cercospora zeae-maydis* and *Cercospora zeinaor, Cochliobolus carbonum, Stenocarpella maydis, Puccinia polysora, Magnaporthe oryzae, Cochliobolus miyabeanus, Ascochyta oryzae, Drechslera gigantean, Microdochium albescens, Cercospora oryzae, Puccinia graminis* f.sp. *oryzae, Uromyces coronatus, Ramularia oryzae, Bipolaris setariae, Cercospora penniseti, Curvularia penniseti, Dactuliophora elongata, Drechslera dematioidea, Claviceps fusiformis, Exserohilum rostratum, Beniowskia sphaeroidea, Myrothecium roridum, Phyllosticta penicillariae, Pyricularia grisea, Puccinia substriata, Moesziomyces penicillariae, Sclerotium rolfsii, Fusarium moniliforme, Gleocercospora sorghi, Sarocladium strictum* (syns *Acremonium strictum*), *Cephalosporium acremonium, Macrophomina phaseolina, Claviceps africana, Sphacelia sorghi, Fusarium* spp., *Fusarium moniliforme* (syn. *Gibberella fujikuroi*), *F. thapsinum* (syn. *G. thapsina*), *Aspergillus* spp., *Fusarium andiyazi, F. nygamai, Penicillium* spp., *Cercospora sorghi, Passalora fusimaculans* (syn. *Cercospora fusimaculans*), *Setosphaeria turcica* (syns. *Exserohilum turcicum, Helminthosporium turcicum*), *Periconia circinata, Ramulispora sorghicola, Gibberella fujikuroi* (syns. *Fusarium moniliforme* var. *subglutinans G. fujikuroi* var. *subglutinans, G. intermnnedia, F. proliferatum*), *Ascochyta sorghi, Puccinia purpurea, Sclerotium rolfsii* (syn. *Athelia rolfsii*), *Ramulispora sorghi, Phyllachora sacchari, Bipolaris sorghicola* (syns. *B. cookei, Helminthosporium cookei*.), *Gloeocercospora sorghi*, or a combination thereof. The at least one fungal plant pathogen may be *Sclerotinia sclerotiorum*. The at least one fungal plant pathogen may be the apothecia of the at least one fungal plant pathogen. The apothecia may be at least one airborne ascospore or conidiospore released from the apothecia.

The sample may be captured in a high throughput ascospore trap.

The present disclosure also provides a use of the herein described biosensor for detecting the presence of and/or the amount of at least one fungal plant pathogen in a sample. The at least one fungal plant pathogen may be *Sclerotinia sclerotiorum*.

The presently disclosed biosensors and methods may be amenable to microfabrication and physical miniaturization and therefore may lower the cost, decrease the size, and may be more capable of automated onsite field monitoring to serve as an early warning system to forecast and manage the outbreaks of fungal plant pathogen diseases, as compared to one or more known methods and devices for monitoring a fungal plant pathogen.

Other aspects and features of the present disclosure will become apparent to those ordinarily skilled in the art upon review of the following description of specific examples in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
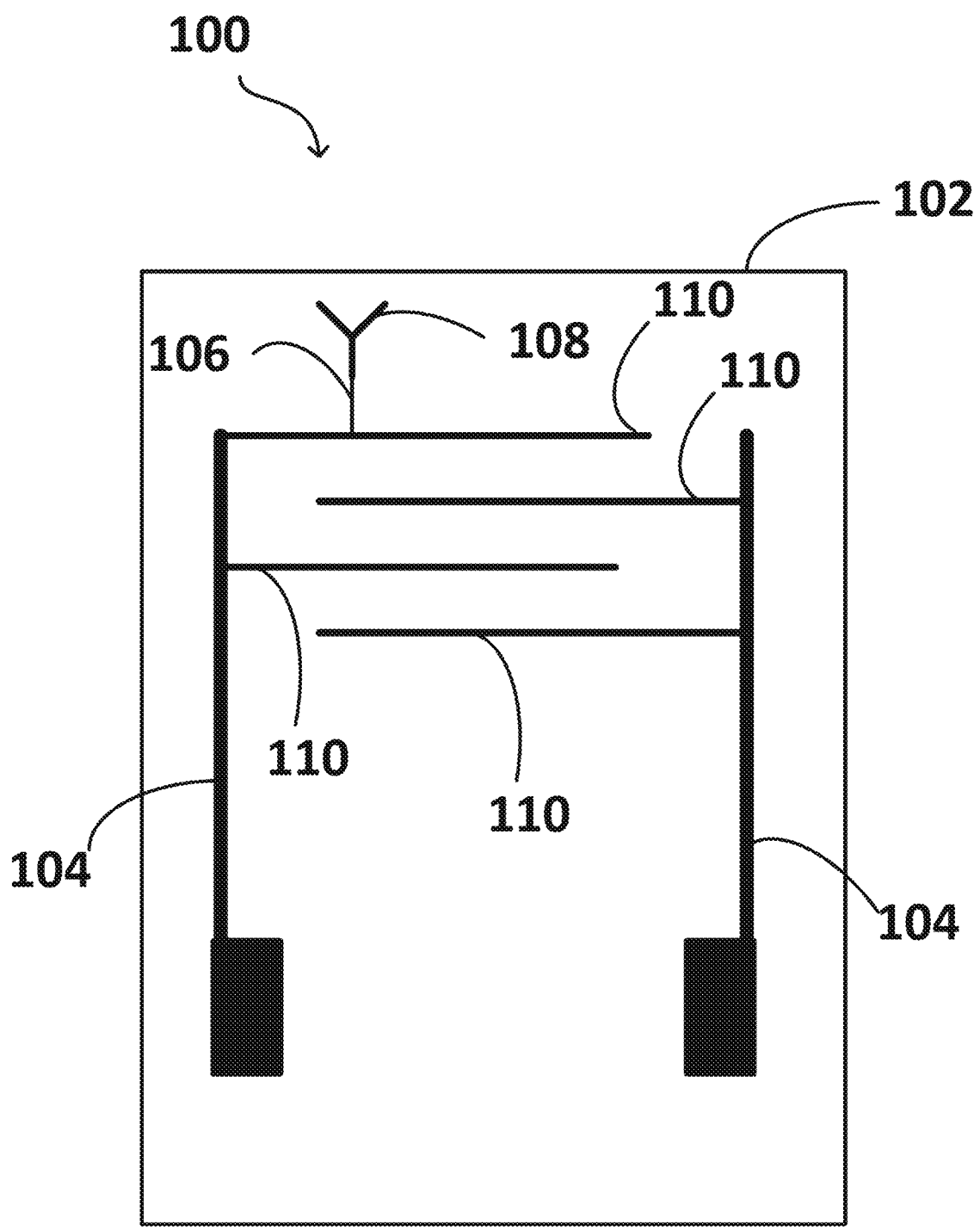
FIG. 1 is an illustration of an example of a biosensor according to the present disclosure.

Generally, the present disclosure provides for a biosensor for detecting the presence of and/or the amount of at least one fungal plant pathogen in a sample, comprising: a support structure; at least two interdigitated electrodes coupled to the support structure, wherein at least one of the interdigitated electrodes is functionalized with a linker coupled to a biological component that recognizes the at least one fungal plant pathogen; and an impedance measurement circuit coupled to the at least two interdigitated electrodes.

The present disclosure also provides a method of making a biosensor for detecting the presence of and/or the amount of at least one fungal plant pathogen in a sample, comprising: contacting an interdigitated electrode with an aqueous solution comprising a linker, for example, 6-mercaptohexanoic acid (MHA) and 11-mercaptoundecanoic acid (MUA), the interdigitated electrode being in electrical communication with at least a second interdigitated electrode; contacting the interdigitated electrode with an aqueous solution comprising 1-Ethyl-3-(3-dimethylaminopropyl) carbodiimide (EDC) and N-hydroxysuccinimide (NHS); contacting the interdigitated electrode with an aqueous solution comprising 3-aminophenylboronic acid (APBA); and contacting the interdigitated electrode with a solution comprising a biological component that recognizes the at least one fungal plant pathogen. In some examples according to the present disclosure, the method further comprises applying a polydimethylsiloxane (PDMS) mask to the interdigitated electrode.

The present disclosure further provides a method of detecting the presence of and/or the amount of at least one fungal plant pathogen in a sample, comprising: measuring the impedance of a biosensor coupled to a biological component that recognizes the at least one fungal plant pathogen; contacting the sample with the biosensor measuring the impedance of the biosensor in contact with the sample; and correlating the change of impedance with the presence and/or the amount of the at least one fungal plant pathogen in the sample.

The present disclosure further provides a method of detecting the presence of and/or the amount of at least one fungal plant pathogen in a sample, comprising: measuring the impedance of a biosensor as presently disclosed; contacting the sample with the biosensor measuring the impedance of the biosensor in contact with the sample; and correlating the change of impedance with the presence and/or the amount of the at least one fungal plant pathogen in the sample.

The present disclosure further provides a use of a biosensor as presently disclosed for detecting the presence of and/or the amount of at least one fungal plant pathogen in a sample.

The biosensor may be any device that combines a biological component capable of interacting with, binding, and/or recognizing at least one fungal plant pathogen in a sample with a physiochemical sensor capable of measuring impedance.

The at least one fungal plant pathogen may be any pathogen that infects a crop plant, for example, a canola plant, a wheat plant, a barley plant, a corn plant, a rice plant, a millet plant, a sorghum plant, or a combination thereof. In some preferred examples according to the present disclosure, the at least one fungal plant pathogen infects more than one type of crop plant, for example, *Sclerotinia sclerotiorum*.

In some examples according to the present disclosure, the at least one fungal plant pathogen infects wheat and barley plants and causes scab, *fusarium* head blight, leaf rust including black, brown, and yellow rust, black stem rust, powdery mildew, canker, tan spot, flag smut, snow scald, leaf blotch, net blotch, alternaria leaf blight, ergot, black point, eyespot, or a combination thereof. The at least one fungal plant pathogen that infects wheat and barley plants may be *Fusarium graminearum, F. avenaceum, F. poae, F. sporotrichioedes, Puccinia graminis, Puccinia triticina, P. recondite, P. striiformis, Erysiphe graminis* f.sp. *Tritici, Glomerella graminicola* (anamorph *Colletotrichum* graminicola), *Pyrenophora tritici-repentis* (telomorph) and *Drechslera tritici-repentis, Pyrenophora trichostoma, Urocystis agropyri, Sclerotinia borealis, Septoria* spp., *Stagnospora* spp., *Pyrenophora teres* tares, *Pyrenophora teres maculate, Claviceps purpurea, Alternaria* spp., *Heminthosporium* spp, *Psudocercosporella herpotrichoides*, or a combination thereof.

In some examples according to the present disclosure, the at least one fungal plant pathogen infects corn plants and causes leaf blight and stalk rot, ear and kernel rot, leaf rust, black stem rust, black kernel rot, brown spot, grey leaf spot, Northern corn leaf spot, southern leaf blight, white ear rot, root and stalk rot, southern rust, or a combination thereof. The at least one fungal plant pathogen that infects corn plants may be *Glomerella graminicola* (anamorphic), *Colletotrichum graminicola, Fusarium verticillioides, Gibberella zeae, Aspergillus flavus, A. parasiticus, Lasiodiplodia theobromae, Physoderma maydis, Exserohilum turcicum, Cochliobolus heterostrophu, Cercospora zeae-maydis* and *Cercospora zeinaor, Cochliobolus carbonum, Stenocarpella maydis, Puccinia polysora*, or a combination thereof.

In some examples according to the present disclosure, the at least one fungal plant pathogen infects rice plants and causes rice blast, brown spot, collar rot, eyespot, leaf scald, narrow brown leaf spot, rusts, white leaf streak, or a combination thereof. The at least one fungal plant pathogen that infects rice plants may be *Magnaporthe oryzae, Cochliobolus miyabeanus, Ascochyta oryzae, Drechslera gigantean, Microdochium albescens, Cercospora oryzae, Puccinia graminis* f.sp. *oryzae, Uromyces coronatus, Ramularia oryzae*, or a combination thereof.

In some examples according to the present disclosure, the at least one fungal plant pathogen infects millet plants and causes *bipolaris* leaf spot, *cercospora* leaf spot, *curvularia* leaf spot, *dactuliophora* leaf spot, *drechslera* leaf spot, ergot, *exserohilum* leaf blight, false mildew, Head mold, *myrothecium* leaf spot, *phyllosticta* leaf blight, *pyricularia* leaf spot, rust, smut, southern blight, top rot, zonate leaf spot, or a combination thereof. The at least one fungal plant pathogen that infects millet plants may be *Bipolaris* setariae, *Cercospora penniseti, Curvularia penniseti, Dactuliophora elongata, Drechslera dematioidea, Claviceps fusiformis, Exserohilum rostratum, Beniowskia sphaeroidea, Myrothecium roridum, Phyllosticta penicillariae, Pyricularia grisea, Puccinia substriata, Moesziomyces penicillariae, Sclerotium rolfsii, Fusarium moniliforme, Gleocercospora sorghi*, or a combination thereof.

In some examples according to the present disclosure, the at least one fungal plant pathogen infects sorghum plants and causes *acremonium* wilt, ergot, uematsu, *fusarium* head blight, root and stalk rot, grain storage mold, gray leaf spot, ladder leaf spot, leaf blight, milo disease (*periconia* root rot), oval leaf spot, pokkah boeng (twisted top), rough leaf spot, rust, southern sclerotial rot, sooty stripe, tar spot, target leaf spot, zonate leaf spot and sheath blight, or a combination thereof. The at least one fungal plant pathogen that infects sorghum plants may be *Sarocladium strictum* (syns *Acremonium strictum*), *Cephalosporium acremonium, Macrophomina phaseolina, Claviceps africana, Sphacelia sorghi, Fusarium* spp., *Fusarium moniliforme* (syn. *Gibberella fujikuroi*), *F. thapsinum* (syn. *G. thapsina*), *Aspergillus* spp., *Fusarium andiyazi, F. nygamai, Penicillium* spp., *Cercospora sorghi, Passalora fusimaculans* (syn. *Cercospora fusimaculans*), *Setosphaeria turcica* (syns. *Exserohilum turcicum, Helminthosporium turcicum*), *Periconia circinata, Ramulispora sorghicola, Gibberella fujikuroi* (syns. *Fusarium moniliforme* var. *subglutinans G. fujikuroi* var. *subglutinans, G. intermedia, F. proliferatum*), *Ascochyta sorghi, Puccinia purpurea, Sclerotium rolfsii* (syn. *Athelia rolfsii*), *Ramulispora sorghi, Phyllachora sacchari, Bipolaris sorghicola* (syns. *B. cookei, Helminthosporium cookei.*), *Gloeocercospora sorghi*, or a combination thereof.

In the context of the present disclosure, reference to the fungal plant pathogen refers to its entire life cycle. For example, *Sclerotinia sclerotiorum* refers to the fungus, the produced *sclerotium*, and the produced apothecia. *Sclerotinia sclerotiorum* can also be known as cottony rot, watery soft rot, stem rot, drop, crown rot and blossom blight.

The sample may be any medium in which one or more fungal plant pathogens may reside and be capable of being recognized by at least one biological component. In some examples according to the present disclosure, the sample is a solution.

The biological component is any compound that is capable of interacting with, binding, and/or recognizing at least one fungal plant pathogen in a sample and is capable of coupling to at least one of the interdigitated electrodes. The biological component may be an antibody or fragment thereof. The antibody may be a polyclonal or a monoclonal antibody. In some preferred examples according to the present disclosure, the biological component is an antibody that recognizes and binds *Sclerotinia sclerotiorum*. The antibody fragment thereof may be an antigen-binding (Fab) or a single-chain variable fragment. In some examples according to the present disclosure, the biological component recognizes and binds to at least one fungal plant pathogen with a dissociation constant (Kd) less than or equal to a micromolar (μM), for example, a nanomolar (nM). Preferably, the biological component recognizes and specifically binds to at least one fungal plant pathogen with a dissociation constant (Kd) less than a nanomolar (nM).

A skilled person would be able to produce an antibody that specifically binds to at least one of the herein described fungal plant pathogens. Antibodies have been successfully produced in rabbits and rats against fungal spores, for example, *Mycosphaerella brassicicola* (Kennedy and Wakeham, 2002 New Methods for Detecting and Enumerating Fungal Spores of Plant Pathogens. Plant Protect. Sci., 38 (Special Issue 1): 38-42; incorporated by reference), *Glomus monosporum* (Göbel, C., Hah., A., Hock, B., 1995. Production of polyclonal and monoclonal antibodies against hyphae from arbuscular mycorrhizal fungi. Crit Rev Biotechnol. 1995; 15 (3-4):293-304; incorporated by reference), *Clostridium tyrobutyricum* (María Lavilla, Ruth de Luis, Celia Conesa, María D. Pérez, Miguel Calvo & Lourdes Sanchez. 2008. Production of polyclonal antibodies against spores of *Clostridium tyrobutyricum*, a contaminant affecting the quality of cheese: characterisation of the immunodominant protein. Food and Agricultural Immunology 19 (1):77-91; incorporated by reference), and Aflatoxigenic Molds (R. Shapira et al., Development of Polyclonal Antibodies for Detection of Aflatoxigenic Molds Involving Culture Filtrate and Chimeric Proteins Expressed in *Escherichia coli*. APPLIED AND ENVIRONMENTAL MICROBIOLOGY 63(3): 990-995; incorporated by reference), and *Stachybotrys chartarum* (Schmechel D & Lewis DM. 2001. The production of species-specific monoclonal antibodies (Mabs) against the allergenic and toxigenic fungus *Stachybotrys chartarum*. The FASEB Journal, Vol. 15(4), p. A662, Abstract #523.1; incorporated by reference).

The support structure may be any solid semiconductor material that is capable of serving as a substrate onto which at least two interdigitated electrodes can be coupled. In some examples according to the present disclosure, the support structure is a silicon wafer or a glass substrate.

At least one of the at least two interdigitated electrodes may be any comb-shaped metallic conductor that is capable of coupling to at least one fungal plant pathogen and is in electrical communication with at least another of the at least two interdigitated electrodes. In some examples according to the present disclosure, a pair of interdigitated electrodes may be orientated to interlock the fingers of their comb-shapes. In the context of the present disclosure, in electrical communication refers to any connection that allows electrons to move between the at least two interdigitated electrodes, for example, a copper wire.

In some examples according to the present disclosure, at least one of the at least two interdigitated electrodes is a working electrode and at least another of the at least two interdigitated electrodes is a reference electrode or a counter electrode. The working electrode is any electrical conductor material that is capable of coupling to at least one biological component that interacts with, binds, and/or recognizes at least one fungal plant pathogen. In some examples according to the present disclosure, the working electrode may be coupled to more than one biological component that interacts with, binds, and/or recognizes at least one fungal plant pathogen. Each one of the more than one biological component may interact with, bind, and/or recognize the same fungal plant pathogen or at least two of the more than one biological component may interact with, bind, and/or recognize different fungal plant pathogens, for example, the working electrode may be coupled to biological components that are capable of interacting with, binding, and/or recognizing 2, 3, 4, 5, 6, 7, 8, 9, or 10 different fungal plant pathogens. The reference electrode is any electrical conductor material that is capable of maintaining an approximately fixed, reproducible electrical potential between the electrode and the sample. The counter electrode is any electrical conductor material that supplies a current to the sample to maintain a desired electrode-solution voltage. In some examples according to the present disclosure, the biosensor comprises a working electrode, a reference electrode and a counter electrode. In some examples according to the present disclosure, at least the working electrode is gold plated. In some examples according to the present disclosure, all of the electrodes are gold plated.

A working electrode capable of coupling to at least one biological component that is capable of interacting with, binding, and/or recognizing at least one fungal pathogen refers to any type of molecular assembly that immobilizes at least one biological component to the electrode and orients the at least one biological component so that it can interact with, bind, and/or recognize at least one fungal plant pathogen in a sample. Coupling to at least one biological component refers to any attachment that connects the working electrode to the biological component and allows the biological component to interact with, bind, and/or recognize at least one fungal pathogen in a sample, for example, by a linker. In some examples according to the present disclosure, the working electrode is functionalized with a linker that is capable of coupling to at least one biological component. A skilled person would understand that functionalizing an electrode refers to attaching functional components to the surface of the electrode. The linker may be a Self-Assembled Monolayer (SAM), a macromolecule, or a thin layer of polymer.

The SAM may be any self-assembling monolayer where a portion of the monolayer is capable of coupling to the surface of the electrode and another portion of the monolayer is capable of coupling to at least one biological component. The backbone of the SAM may be an alkane, oligo (ethylene glycol), oligonucleotides, oligopeptides, amino acids (cysteine and methionine), linear polysaccharide (chitosan, hyaluronic acid). The functional groups of SAM may be thiol, silane, phosphonic acid, or carboxylic acid, for example, distal carboxylic acid. These groups may form covalent bonds with gold or hydroxyl groups on the electrode surface and provide an anchoring site for at least one biological component, for example, distal carboxylic acid may covalently conjugate with an aminoalkyl-boronic acid or directly with an amine group (for example a lysine residue of the amine group) of an antibody or fragment thereof that interacts with, binds, and/or recognizes at least one fungal plant pathogen. In some examples according to the present disclosure wherein the working electrode is functionalized with SAM, the head group of the SAM binds to the working electrode and the functional group of the SAM binds to at least one biological component that interacts with, binds, and/or recognizes at least one fungal plant pathogen. In some examples according to the present disclosure, the functional group of the SAM is boronic acid, for example when increasing the sensitivity and stability of the biosensor is desirable. Because of the size of ascospores, it may be desirable to specifically orient the at least one biological component that interacts with, binds, and/or recognizes at least one fungal plant pathogen on the electrode to, for example, increase the density of their paratopes free in the sample and available for binding to the ascospores. In some examples according to the present disclosure, antibodies may be oriented approximately upright with respect to the SAM resulting in their paratopes facing the solution, so that, for example, the antigens may have better access to at least one fungal plant pathogen in the solution and/or to increase the density of the paratopes in the solution.

The thin layer polymer may be any polymer deposited on the surface of the electrode in situ by either chemical or electrochemical means such that a portion of the layer is capable of coupling to at least one biological component. The polymer can be poly[pyrrole-co-3-carboxyl-pyrrole], poly-(carboxybetaine methacrylate), polytyramine, poly (o-phenylenediamine), polytyramine, or terthiophene-carboxyl acid.

In some examples according to the present disclosure wherein the working electrode is functionalized with SAM, the working electrode may be functionalized with a SAM coupled to at least one biological component, for example an antibody, that interacts with, binds, and/or recognizes at least one fungal plant pathogen by: (1) contacting the working electrode with an aqueous solution comprising 6-MHA and 11-MUA; (2) contacting working electrode with an aqueous solution comprising EDC and NHS; (2) contacting the working electrode with an aqueous solution comprising APBA; and (3) contacting the working electrode with a solution comprising at least one biological component that interacts with, binds, and/or recognizes at least one fungal plant pathogen. In some examples according to the present disclosure, contacting the working electrode with a solution refers to submerging at least a portion of the working electrode in the solution, for example, submerging a sufficiently large portion of the working electrode in the solution so that the at least one biological component coupled to the working electrode can interact with, bind, and/or recognize at least one fungal plant pathogen in the sample.

The inventors discovered that using a SAM with a boronic acid surface group to link at least one antibody that interacts with, binds, and/or recognizes at least one fungal plant pathogen to the electrode showed an increased efficiency of binding ascospores compared to using PEG as a linker. Experimental results using alkane and PEG as the backbone of the SAM constituting the insulating layer in the sensor showed that they have a similar effect on the sensor impedance response and hence the sensor sensitivity. However, a combination of 11-Mercaptoundecanoic acid (MUA), and 16-Mercaptohexadecanoic acid (MDA) in the molar ratio of (10:1) as the SAM layer yielded an impedance response higher than those of the other SAMs that have been investigated. In some examples according the present disclosure, a SAM with a boronic acid surface group as a linker may be used instead of a SAM without a boronic acid surface group as a linker, for example when increasing the efficiency of ascospore binding is desirable.

The: (1) number of fingers of each interdigitated electrode; (2) length of each finger; (3) width of each finger; (4) gap between adjacent interdigitated fingers, and (5) thickness of each finger may be varied to alter the signal-to-noise ratio. In some examples according to the present disclosure, the finger length may be from about 0.1 mm to about 5 mm, for example, 0.1 mm; 0.2 mm, 0.4 mm, 0.6 mm, 0.8 mm, 1.0 mm, 1.2 mm, 1.4 mm, 1.6 mm, 1.8 mm, 2.0 mm, 2.2 mm, 2.4 mm, 2.6 mm, 2.8 mm, 3.0 mm, 3.2 mm, 3.4 mm, 3.6 mm, 3.8 mm, 4.0 mm, 4.2 mm, 4.4 mm, 4.6 mm, 4.8 mm, 5.0 mm, or the length is from any one of the lengths listed above to any other of the lengths listed above. In some examples according to the present disclosure, the width of each finger and/or the gap between adjacent interdigitated fingers may be varied to accommodate the size of at least one plant fungal pathogen in the sample. In some examples according to the present disclosure, the width of each finder and/or the gap between adjacent interdigitated fingers may be, independently, from about 2 µm to about 20 µm, for example, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, or the distance is from any one of the distances listed above to any other of the distances listed above. In some examples according to the present disclosure, the length of the fingers and the number of finger pairs are decreased to increase the sensitivity of the electrode. In some examples according to the present disclosure, the fingers of a pair of interdigitated electrodes, together, make up an about square shape. The about square shape may have a length and width of from about 1 mm to about 50 mm, for example, about 1 mm; about 2 mm; about 3 mm; about 4 mm; about 5 mm; about 6 mm; about 7 mm; about 8 mm; about 9 mm; about 10 mm; about 15 mm; about 20 mm; about 25 mm; about 30 mm; about 35 mm; about 40 mm; about 45 mm; or the distance is from any one of the distances listed above to any other of the distances listed above. In some examples according to the present disclosure, the thickness of each finger may be from about 25 nm to about 400 nm, for example, about 25 nm; about 50 nm; about 75 nm; about 100 nm; about 110 nm; about 125 nm; about 150 nm; about 175 nm; about 200 nm; about 250 nm; about 300 nm; about 350 nm; about 400 nm; or the distance is from any one of the thicknesses listed above to any other of the thicknesses listed above. In some examples according to the present disclosure, the about square shape has a length of about 3 mm, a width of about 3 mm, a thickness of about 110 nm, and the gap between the fingers is about 3 µm.

The interdigitated electrodes coupled to the support structure refers to any type of fastening of the electrodes to the support structure that maintains the electrodes' orientation on the support structure during the process of detecting at least one fungal plant pathogen. In some examples according to the present disclosure, the electrodes are laminated onto the support structure using a photolithography process.

An impedance measurement circuit is any voltage or current source and any voltage or current analyzer connected in an electrical path in which electrons may flow. In some examples according to the present disclosure, the impedance measurement circuit comprises a potentiostat in electrical communication with the at least two interdigitated electrodes.

Measuring the impedance refers to applying a current or voltage excitation perturbation in an electrochemical cell and measuring the voltage or the current response as a function of an applied excitation frequency. Impedance is a measure of the opposition to the flow of current, arising from ion diffusion, electrode kinetics, redox reactions, and molecular interactions at the electrode surface, when an alternating excitation voltage is applied to the cell.

Without being limited by theory, it is believed that in the presently disclosed non-Faradaic based biosensor, contributions from the electrolyte resistance and the interfacial capacitances dominate the impedance of the system. The interfacial capacitances are sensitive to the probe-analyte binding occurring on the surface of the electrode and can be used for detection and quantification of target antigens. The total capacitance ($C_{tot}$) of a sensor electrode may be considered as a combination of capacitances attributed to the SAM ($C_{SAM}$), recognition layer ($C_{REC}$), and double layer ($C_{DL}$) connected in series [12-20].

$$\frac{1}{C_{tot}} = \frac{1}{C_{SAM}} + \frac{1}{C_{REC}} + \frac{1}{C_{DL}} \quad \text{(Eq. 1)}$$

And the impedance is related to capacitance as:

$$Z_C = \frac{1}{j\omega C}, \quad \text{(Eq. 2)}$$

where, $\omega = 2\pi f$, is the angular frequency and f is the applied frequency in hertz.

Due to the reciprocal nature of the relation, the total capacitance of the electrode/electrolyte interface is most sensitive to the changes in the magnitude of the smallest capacitance in the series. As $C_{DL}$ in aqueous solution is normally a large value [21, 22] on the order of µF/cm², a sensitive impedance biosensor may be designed such that the $C_{SAM}$ is also a large value, and $C_{REC}$ is a small value [12-20]. Therefore, surface modification and immobilization of the antibody may play a role in the development of a sensitive impedance based biosensor.

An impedance spectrum may be obtained by applying a current or voltage excitation perturbation in an electrochemical cell, for example, a biosensor according to the present disclosure in a sample, and measuring the voltage or the current response as a function of the applied excitation frequency.

In some examples according to the present disclosure, correlating the change of impedance with the present and/or the amount of at least one fungal plant pathogen in the sample comprises correlating the change of impedance with a standard curve of known impedances of known amounts of the at least one fungal plant pathogen in the sample.

In some examples according to the present disclosure, the biosensors may be in electrical communication with a processor that automates the detection of at least one fungal plant pathogen. In some examples according to the present disclosure, the biosensors may be coupled to a high throughput ascospore trap and used to forecast of the outbreak of crop plant infection. For example, in the case of Sclertonia stem rot, the threshold number of ascospore [4] in the air which allows an 8-day advanced forecasting of the outbreak of Sclerotinia stem rot is about 9 ascospores/m$^3$. By preconcentrating the ascospores with a spore trap, the presently disclosed biosensors may be used for detecting and forecasting Sclerotinia stem rot outbreak and/or serving as an early warning system for the management and control of Sclerotinia stem rot of canola.

FIG. 1 illustrates an example of a biosensor according to the present disclosure. The biosensor (100) comprises: a support structure (102); at least two interdigitated electrodes coupled to the support structure (104), wherein at least one of the interdigitated electrodes (104) is functionalized with a linker (106) coupled to a biological component that interacts with, binds, and/or recognizes at least one fungal plant pathogen (108); and an impedance measurement circuit coupled to the at least two interdigitated electrodes (now shown). The at least two interdigitated electrodes (104) each comprise two fingers (110).

Figure 2:
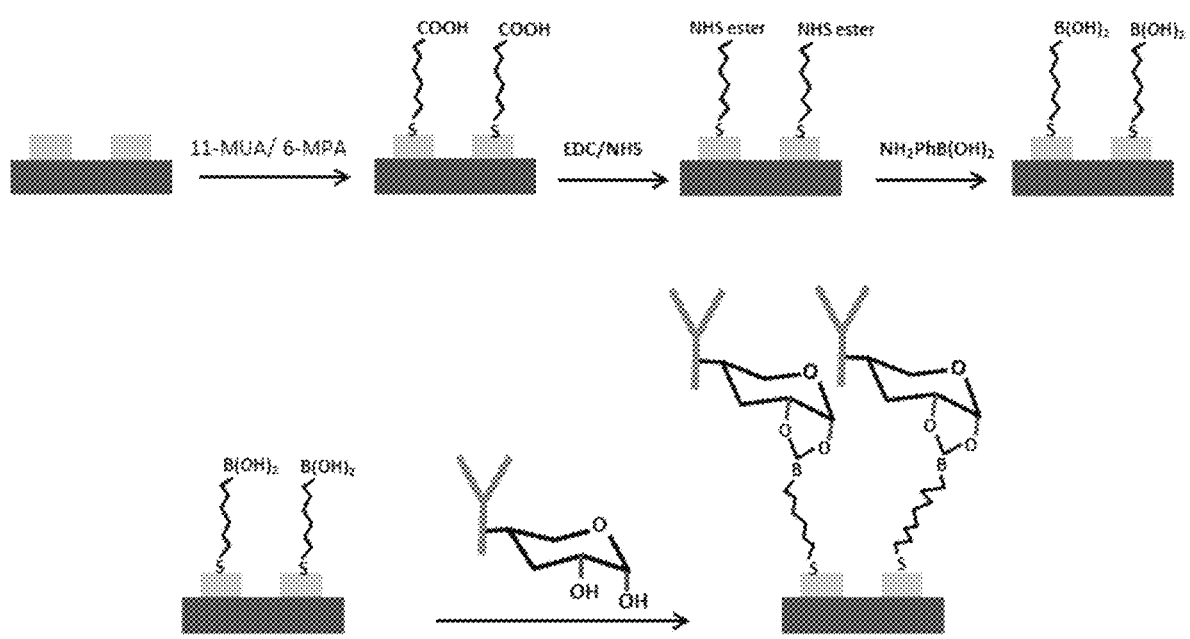
FIG. 2 is an illustration of a method of making a biosensor according to the present disclosure.

FIG. 2 illustrates an example of surface functionalization steps and a process to achieve oriented immobilization of at least one antibody that interacts with, binds, and/or recognizes at least one fungal plant pathogen on the surface of at least one electrode. The first step in the functionalization of the gold surface of the IDE is the formation of a SAM with carboxylic acid end groups. Thiols with different chain lengths, viz 11-MUA and 6-MHA aqueous ethanol solution in molar ratio of 1:10, may be used to form a SAM layer to reduce steric crowding of the surface carboxylic acid end group. Treatment of the surface with EDC/NHS solution may activate the carboxylic acid group by the formation of NHS ester which can efficiently react with amino group of APBA to form surface boronic acid group. Cyclic boronate esters may form when boronic acid reacts with the 1,2- or 1,3-diol group of the carbohydrate moiety present in the fragment crystalizable region (Fc) of the antibody [8,9,10, 11]. As the Fc region is located far away from the at least one antibody binding sites and the boronate ester formation is specific to the carbohydrate moiety, the immobilization reaction afforded by boronic acid functionalized electrode may provide a well oriented antibody with its paratopes facing the solution and readily available for efficient binding with at least one fungal plant pathogen in a sample.

EXAMPLES

Example 1—Materials and Reagents

1-Mercapto-11-undecanoic acid 97% (11-MUA), 1-Mercapto-6-hexanoic acid 90% (6-MHA), N-(3-(dimethylamino)propyl)-N'-ethylcarbodiimide hydrochloride (EDC), N-hydroxysuccinimide 98% (NHS), 3-3-aminophenylboronic acid monohydrate 98% (APBA), Ethanol (100%), disodium hydrogen phosphate, monosodium hydrogen phosphate, and bovine serum albumin 98% (BSA) were purchased from Sigma-Aldrich Canada Co. (Oakville, Ontario) and were used without further purification. Ultrapure water (18.2 MΩ/cm) obtained from Millipore equipment (Mili-Q water) for sample preparation and washing.

Polyclonal anti-Sclerotinia sclerotiorum antibody was produced by Cedarlane lab following a standard procedure from rabbits using Sclerotinia sclerotiorum as the antigen. Ascospores of Sclerotinia sclerotiorum were produced using a standard method (InnoTech Alberta accession #184) by planting sclerotia, generated from sliced carrot roots, into a wet sand and incubating at 10° C. until the sclerotia germinates to form apothecia. The ascospores released from the apothecia were harvested by trapping onto a filter paper disc by applying vacuum.

Example 2—Gold IDE Sensor Chip and Polydimethylsiloxane (PDMS) Mask

Figure 3A:
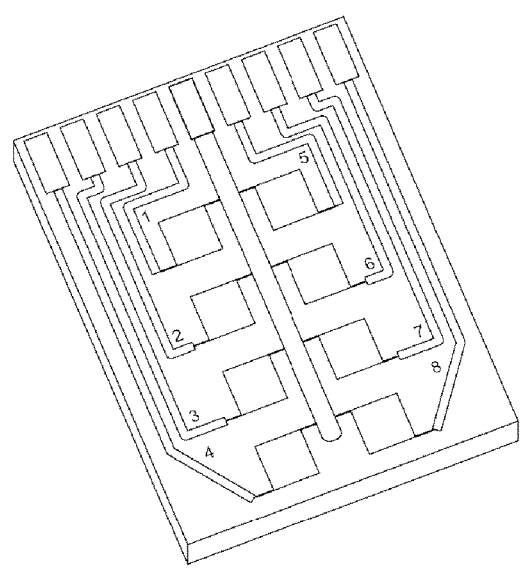
FIGS. 3A-B are illustrations produced from photographs of an example of a biosensor according to the present disclosure.

A custom designed IDE sensor chip, with digit parameters optimized for nanoparticle-enhanced impedimetric sensors [23], was fabricated on a silicon wafer with 500 nm thermal oxide following a standard photolithography process flow involving sputter deposition of chromium (10 nm) and gold (100 nm), photoresist and photomask patter transfer followed by development, reactive ion etching and lift-off. Each of the sensor chips has eight 3 mm×3 mm square IDEs with digit length, width, thickness, and gap of 3 mm, 3 μm, 110 nm, and 3 μm respectively. Illustrations of a typical sensor chip are displayed in FIGS. 3A and B.

Figure 3B:
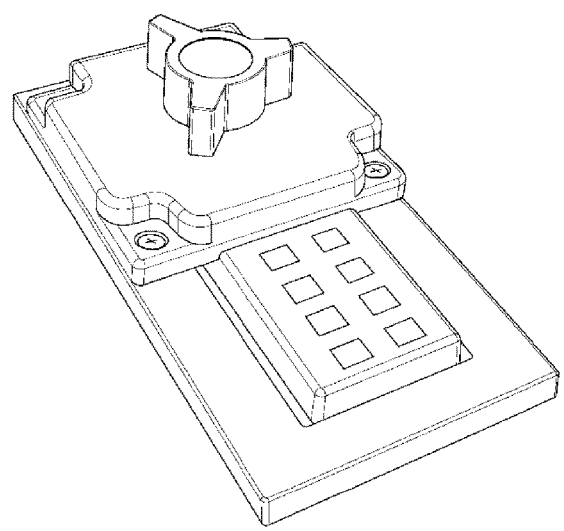

To facilitate functionalization of the IDE surface without affecting other areas of the chip, a PDMS mask, as shown in FIG. 3B, with eight units of 3 mm×3 mm square wells, designed to fit the IDEs on the sensor chip was custom designed and fabricated in the lab. The PDMS mask allows independent and localized modification of each IDE on a sensor chip with any desired modifying solutions.

Example 3—Protocols for Surface Functionalization

The chips used for surface functionalization were cleaned by sonicating for about 5 minutes each in acetone, isopropanol, Millipore water (MPW) and then drying with a stream of nitrogen. The chips were then exposed to Argon plasma (1 Torr Ar atmosphere, 18 W high RF) for 5 minutes to ablate any adsorbed organic materials on the surface. The freshly cleaned IDEs of the chip were functionalized in a sequence of successive reaction steps by submerging them in different solutions using the PDMS mask as presented in FIGS. 3A and B. After each functionalization reaction step, the IDEs were washed with the solvents used to prepare the solutions including ethanol, 10 mM PBS at pH 7.4 and/or MPW to remove any chemicals not covalently bound to the surface.

The affinity of thiol with gold was utilized to form an insulating self-assemble monolayer (SAM) with distal carboxylic acid group on the surface of the IDEs. The reaction was carried out by submerging the IDE overnight at 4° C. in a 50 μL of 10 mM 6-MHA and 1 mM 11-MUA in 95% aqueous ethanol solution. After washing thoroughly with ethanol and MPW, the SAM modified IDEs were submerged in a 50 μL of 0.1 M EDC and 0.1 M NHS aqueous solution for 20 mins. The IDEs were washed and submerged in a 50 μL of 52 mM APBA solution (10 mM PBS at pH 7.4) for 3 hrs. The boronic acid functionalized IDEs were submerged overnight in 50 μL of 5 μg/ml anti-Sclerotinia sclerotiorum antibody buffered solutions (10 mM PBS at pH 7.4).

Example 4—Instruments

Electrochemical Impedance Spectroscopy (EIS) measurements were performed with a potentiostat/galvanostat SP-200 controlled by EC lab software from BioLogic Scence Instruments Inc (Knoxville, Tenn.). A custom built electrical contact pad and connector, as shown in FIG. 3B, was used to make electrical connections between SP-200 and the IDEs on the sensor chips. A PDMS mask with eight wells was used to submerse the IDEs of the sensor chip with 50 μL of 10 μM PBS at pH 7.4 for impedance spectra measurements. Impedance spectra were measured by applying 10 mV sinusoidal excitation perturbation at 0 V DC in the frequency range of 10 Hz to 1 MHz.

A digital optical microscope, VHX-700F from KEYENCE Canada Inc. (Mississauga, Ontario), was used for imaging and estimating the number of ascospores captured on the surface of the IDEs. A Hemocytometer and Motic AE 31. The number of spores suspended in the solution and hence the concentration was determined by using a Hemocytometer and an inverted Biological Microscope (Carlsbad, California) combination. The microscope is used to visualize and count the number of spores in the Hemocytometer which is a counting chamber containing the spore solution of interest. The IDE sensors were incubated in solutions with known spore concentrations determined above. The number of spores captured on the IDE sensors were determined by a digital optical microscope, VHX-700F from KEYENCE Canada Inc. (Mississauga, Ontario).

Figure 4:
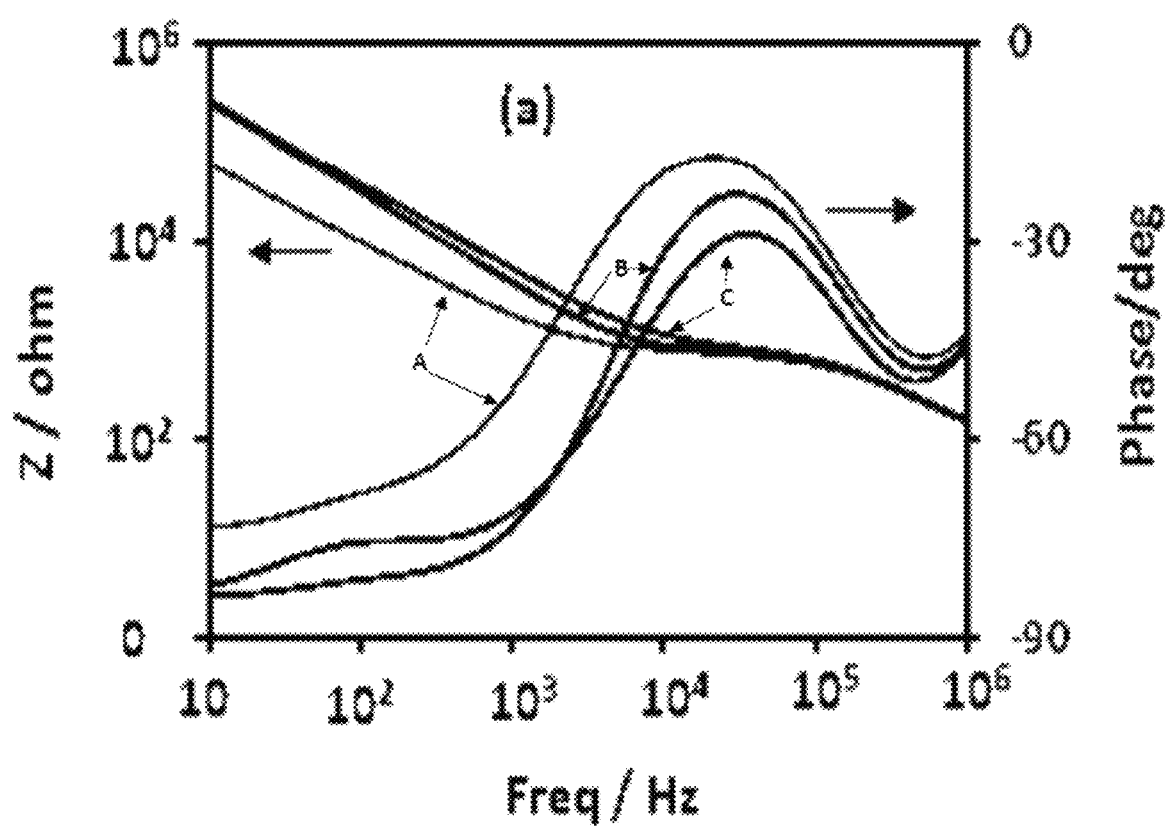
FIG. 4 is a graph of a plot of impedance magnitude and phase verses frequency for IDE gold electrodes: (A) bare gold electrode before modification, (B) after SAM modification, and (C) after anti-*Sclerotinia sclerotiorum* antibody immobilization.
Figure 5:
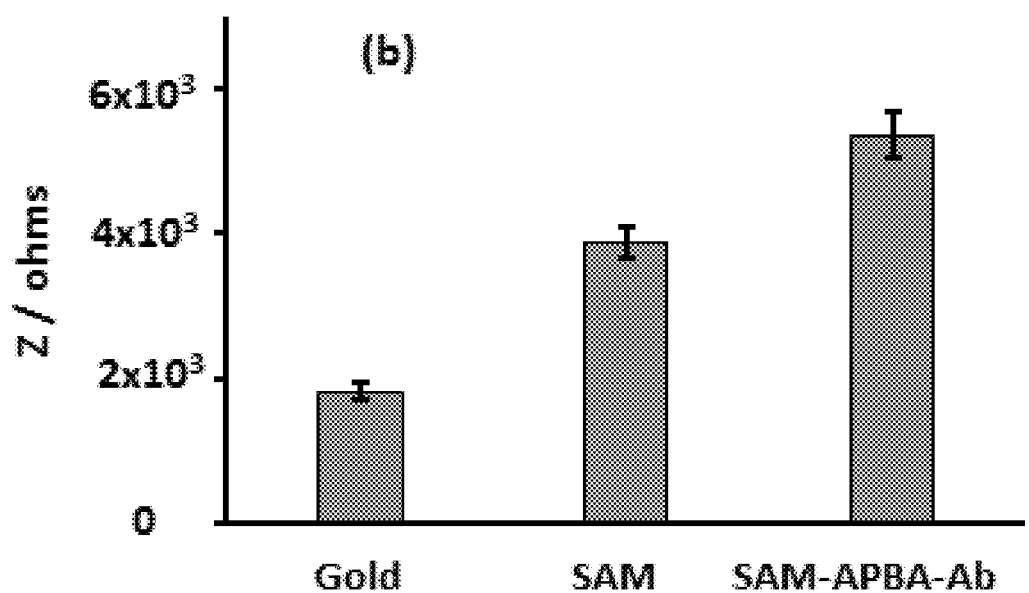
FIG. 5 is a graph of a plot of impedance magnitude determined at 1000 Hz for an IDE after difference stages of surface modification.

Example 5—Impedance Spectra Illustrating Observed Impedance Following Different Stages of Making a Biosensor According to the Present Disclosure FIG. 4 shows the impedance spectra, the plots of the impedance magnitude and phase versus frequency, of the applied sinusoidal excitation potential (10 mV at 0 V DC) obtained for the interdigitated electrode (IDE) before modification (bare gold), after modification with SAM, and subsequently after immobilization of anti-*Sclerotinia sclerotiorum* antibody. The impedance magnitude of a non-faradaic impedance spectrum is dominated by interface capacitance, solvent resistance, and dielectric capacitance in the low, intermediate, and high frequency region of the spectrum, respectively [24, 25]. As presented in FIG. 4, these regions of the spectrum are observed in the impedance spectra as expected. It is important to note that the capacitance of the system is better represented by constant phase element as indicated by the magnitude of the phase angle in the low frequency region. As shown in FIG. 4, modification of the bare gold IDE by SAM led to an increase in the impedance, as expected for capacitances connected in series with the double layer, because the SAM layer is composed of low dielectric alkane chains [26]. A further increase in impedance, albeit a smaller change was observed in the subsequent modification of the IDE surface with APBA and anti-*Sclerotinia sclerotiorum* antibody. To illustrate the observed impedance change following different stages of the IDE surface modification, the magnitudes of the impedance recorded at 1000 Hz (in FIG. 4) are plotted in FIG. 5.

The impedance change observed upon conjugation of APBA and anti-*Sclerotinia sclerotiorum* antibody to the covalently attached SAM as displayed in FIG. 4 indicates that the fabricated sensor has the sensitivity to detect the binding of antigens to the surface immobilized antibodies. In the affinity based biosensors, a major source of interfering noise comes from nonspecific binding of biomolecules present in the solution. Although, the nonspecific binding on the sensor surface can be greatly reduced by the formation of SAM layer on the IDE [27] further treatment of the surface with reagents such as a blocking agent is required to minimize their effects. In our biosensor, the IDE after surface modifications and anti-*Sclerotinia sclerotiorum* antibody immobilization was incubated with 2% BSA solution to minimize nonspecific binding prior to treatment with the target ascospore solution.

Figure 6A:
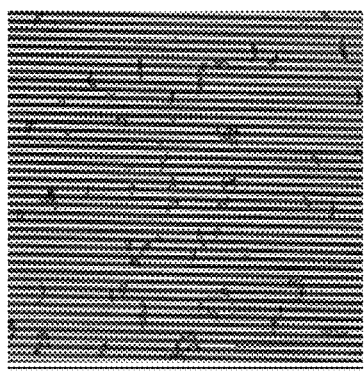
FIGS. 6A-C are optical images of ascospores selectively captured by immobilized anti-*Sclerotinia sclerotiorum* antibodies on SAM modified IDE surface. The number of ascospores on the surfaces i.e. ascospores/cm$^2$ are (FIG. 6A) $(1.1\pm0.1)\times10^5$, (FIG. 6B) $(4.4\pm0.4)\times10^4$, and (FIG. 6C) $(2.5\pm0.3)\times10^4$. Scale bar equals 100 μm.
Figure 6B:
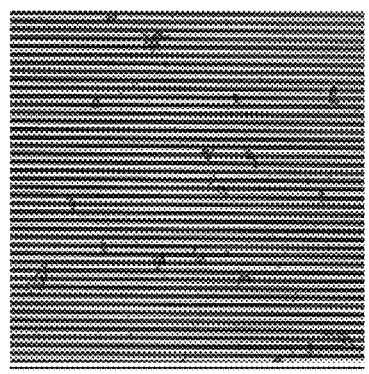
Figure 6C:
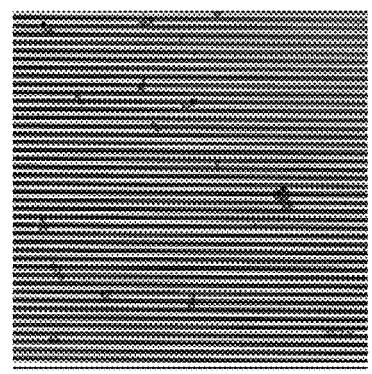

FIGS. 6A-C show the optical microscopy images of the ascospores selectively captured from ascospores in solution, via antigen-antibody affinity binding, by the immobilized antibodies on the surface of the IDE. The number of ascospores on the surfaces i.e. ascospores/cm$^2$ are (FIG. 6A) $(1.1\pm0.1)\times105$, (FIG. 6B) $(4.4\pm0.4)\times104$, and (FIG. 6C) $(2.5\pm0.3)\times104$. Scale bar equals 100 μm. It is important to note that the ascospores captured by the immobilized antibodies on the surface of the IDE are unaffected by repeated washing, indicating suitability of the boronic ester bond for antibody immobilization [8, 9, 10, 11]. As the ellipsoidal shaped ascospore has a size in the range, 4-6 μm×9-14 μm [28], a digital optical microscope was used in this work as a technique to verify the efficacy of the protocol used to capture ascospores by the immobilized antibodies.

The microscopic images were also used for determining the number of ascospores captured on the IDE surface and to correlate their contributions to the impedance response. As shown in FIGS. 6A-C, the estimated number of ascospores in the representative images correspond to about 9700, 4000 and 2300 ascospores captured on the surfaces of 3 mm×3 mm IDEs in sensor chip. The numbers or concentrations of ascospores in the solution were determined by using a hemocytometer. From the concentration of ascospores in the solution and the observed number ascospores captured on the surface of the IDE, the inventors have determined that the antibody-target antigen binding proceeds with high efficiency and most of the ascospores present in the solution captured on the surface of the IDE.

Figure 7:
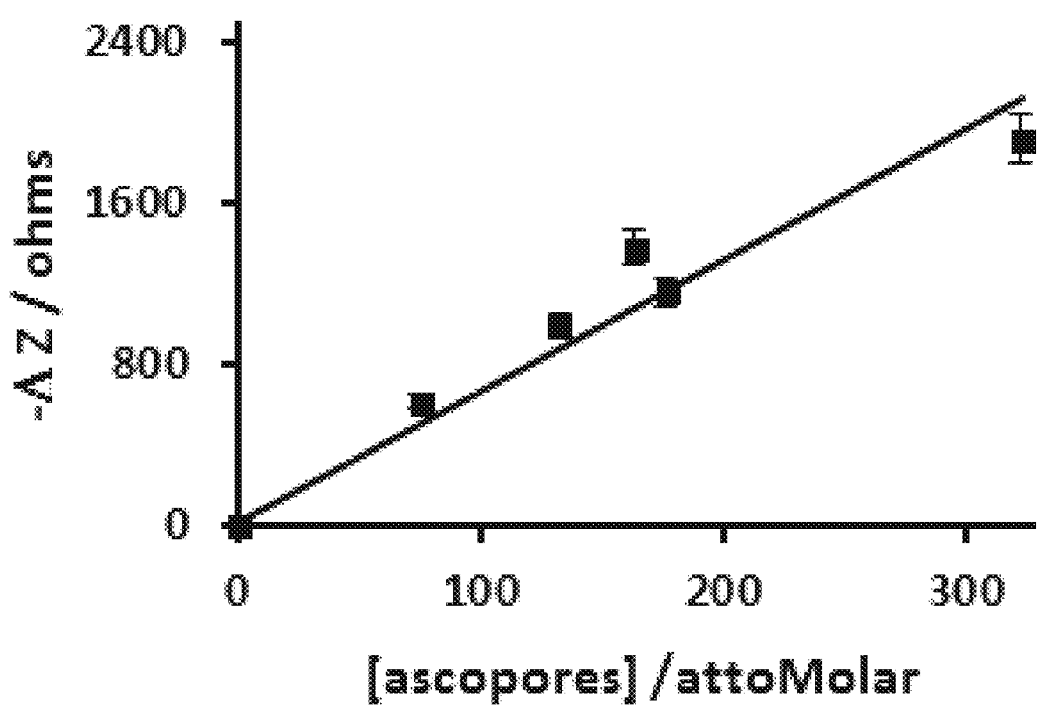
FIG. 7 is a graph of a plot of impedance change ($\Delta Z$) versus ascospore concentration [ascospore] in the incubation solution. The black line is the linear fit to the experimental data point (filled squares), error bars are RSD (n=4). Where, $\Delta Z = Z_{Ab-Sp} - Z_{Ab}$, and $Z_{Ab}$ and $Z_{Ab-Sp}$ are the magnitudes of the impedance measured at 1000 Hz before and after the ascospores have been captured by the immobilized anti-*Sclerotinia sclerotiorum* antibodies on the surface of modified IDE.

Example 6—Impedance Based Biosensor is Suitable for Sensitive Detection of Ascospores FIG. 7 shows the plot of impedance change ($\Delta Z$) versus ascospores concentration [ascospore] in the incubation solution. The black line is the linear fit to the experimental data point (filled squares), error bars are RSD (n=4). Where, $\Delta Z = Z_{Ab-Sp} - Z_{Ab}$, and $Z_{Ab}$ and $Z_{Ab-Sp}$ are the magnitudes of the impedance measured at 1000 Hz before and after the ascospores have been captured by the immobilized anti-*Sclerotinia sclerotiorum* antibodies on the surface of modified IDE.

The impedance change ($\Delta Z$) at any given ascospore concentration was calculated from the impedance spectra of an IDE recorded before ($Z_{Ab}$) and after ($Z_{Ab-Sp}$) the capture of the ascospores by the immobilized anti-*Sclerotinia sclerotiorum* antibodies on the surface of functionalized IDE. Binding of the ascospores on the IDE surface led to a decrease in impedance magnitude, thereby yielding a negative value for the impedance change, $\Delta Z = Z_{Ab-Sp} - Z_{Ab}$, calculated from the impedance magnitude at the applied sinusoidal AC frequency of 1000 Hz. As demonstrated by the experimental data plotted in FIG. 7, the impedance magnitude decreases with increase in the number of bound ascospores on the surface of the IDE.

The change in the magnitude of impedance in a capacitive based sensor due to affinity binding of target antigens to the surface immobilized antibodies can arise from the dielectric properties of the target antigens, the displacement of water molecules due the target binding, and the change in the thickness of the recognition layer [12-21]. These changes contribute to impedance change via the capacitance of the recognition layer ($C_{REC}$) in the biosensor.

A unique advantage of working with ascospores is their size [28] (4-6 μm×9-14 μm) which allowed us to confirm the selective capture of ascospores on the sensor surface using optical microscope (FIGS. 6A-C). Further, the optical images were used to estimate the number ascospores captured on the IDE surface which in turn is related to the concentration of ascospores in the incubation solutions and these concentration values were plotted as shown in FIG. 7. Hence, these results allowed the inventors to obtain a direct and unambiguous correlation between the number of selectively captured ascospores and their impedance response.

The experimental data in FIG. 7 can be fitted with a linear regression ($R^2$=93%) to yield a slope of 6.5 ohms/aM ascosproes in the solution. The limit of detection (LOD) evaluated from the signal-to-noise ratio determined from the standard deviations of the negative controls was about 130 aM.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

[1] Kutcher, H. R. & Wolf, T. M. Low-drift fungicide application technology for *sclerotinia* stem rot control in canola. Crop Protection 25, 640-646 (2006).

[2] McLaren, D. L. et al. Predicting diseases caused by *Sclerotinia sclerotiorum* on canola and bean—a western Canadian perspective. Canadian Journal of Plant Pathology 26, 489-497 (2004).

[3] Bom, M. & Boland, G. J. Evaluation of disease forecasting variables for *sclerotinia* stem rot (*Sclerotinia sclerotiorum*) of canola. Canadian Journal of Plant Science 80, 889-898 (2000).

[4] Parker, M. L., McDonald, M. R. & Boland, G. J. Evaluation of Air Sampling and Detection Methods to Quantify Airborne Ascospores of *Sclerotinia sclerotiorum*. Plant Disease 98, 32-42 (2014).

[5] Ziesman, B. R., Turkington, T. K., Basu, U. & Strelkov, S. E. A Quantitative PCR System for Measuring *Sclerotinia sclerotiorum* in Canola (*Brassica napus*). Plant Disease 100, 984-990 (2015).

[6] Almquist, C. & Wallenhammar, A. C. Monitoring of plant and airborne inoculum of *Sclerotinia sclerotiorum* in spring oilseed rape using real-time PCR. Plant Pathology 64, 109-118 (2015).

[7] Jones, S., Pilkington, S., Gent, D., Hay, F. & Pethybridge, S. A polymerase chain reaction assay for ascosporic inoculum of *Sclerotinia* species. New Zealand Journal of Crop and Horticultural Science 43, 233-240 (2015).

[8] Duval, F., van Beek, T. A. & Zuilhof, H. Key steps towards the oriented immobilization of antibodies using boronic acids. The Analyst 140, 6467-6472 (2015).

[9] Ho, J. an A. et al. Ultrasensitive electrochemical detection of biotin using electrically addressable site-oriented antibody immobilization approach via aminophenyl boronic acid. Biosensors and Bioelectronics 26, 1021-1027 (2010).

[10] Abad, J. M. et al. Immobilization of peroxidase glycoprotein on gold electrodes modified with mixed epoxyboronic acid monolayers. Journal of American Chemical Society 124, 12845-12853 (2002).

[11)] Adak, A. K. et al. Fabrication of antibody microarrays by light-induced covalent and oriented immobilization. ACS Applied Materials and Interfaces 6, 10452-10460 (2014).

[12] Luo, X. & Davis, J. J. Electrical biosensors and the label free detection of protein disease biomarkers. Chemical Society Reviews 42, 5944 (2013).

[13] Tsouti, V., Boutopoulos, C., Zergioti, I. & Chatzandroulis, S. Capacitive microsystems for biological sensing. Biosensors and Bioelectronics 27, 1-11 (2011).

[14] Guan, Jian-Gao. Miao, Yu-Qing., Zhang, Q.-J. Impedimetric Biosensors. Journal of Bioscience and Bioengineering 97, 219-226 (2004).

[15] Lisdat, F. & Schafer, D. The use of electrochemical impedance spectroscopy for biosensing. Analytical and Bioanalytical Chemistry 391, 1555-1567 (2008).

[16] Prodromidis, M. I. Impedimetric immunosensors-A review. Electrochimica Acta 55, 4227-4233 (2010).

[17] Bonanni, A. & Del Valle, M. Use of nanomaterials for impedimetric DNA sensors: A review. Analytica Chimica Acta 678, 7-17 (2010).

[18] Daniels, J. S. & Pourmand, N. Label-free impedance biosensors: Opportunities and challenges. Electroanalysis 19, 1239-1257 (2007).

[19] Randviir, E. P. & Banks, C. E. Electrochemical impedance spectroscopy: an overview of bioanalytical applications. Analytical Methods 5, 1098 (2013).

[20] Berggren, C., Bjamason, B. & Johansson, G. Capacitive biosensors. Electroanalysis 13, 173-180 (2001).

[21] Liu, J., Chisti, M. M. & Zeng, X. General Signal Amplification Strategy for Nonfaradic Impedimetric Sensing: Trastuzumab Detection Employing a Peptide Immunosensor. Analytical Chemistry 89, 4013-4020 (2017).

[22] Mirsky, V. M., Riepl, M. & Wolfbeis, O. S. Capacitive monitoring of protein immobilization and antigen-antibody reactions on monomolecular alkylthiol films on gold electrodes. Biosensors and Bioelectronics 12, 977-989 (1997).

[23] Mackay, S., Hermansen, P., Wishart, D. & Chen, J. Simulations of Interdigitated Electrode Interactions with Gold Nanoparticles for Impedance-Based Biosensing Applications. 22192-22208 (2015). doi:10.3390/s150922192.

[24] Guimerà, A. et al. Effect of surface conductivity on the sensitivity of interdigitated impedimetric sensors and their design considerations. Sensors and Actuators, B: Chemical 207, 1010-1018 (2015).

[25] Couniot, N. et al. Lytic enzymes as selectivity means for label-free, microfluidic and impedimetric detection of whole-cell bacteria using ALD-Al2O3 passivated microelectrodes. Biosensors and Bioelectronics 67, 154-161 (2015).

[26] Rickert, J., Gpel, W., Beck, W., Jung, G. & Heiduschka, P. A mixed self-assembled monolayer for an impedimetric immunosensor. *Biosens. Bioelectron.*, 11, (1996) 757-768.
[27] Vaisocherová, H. & Brynda, E. Functionalizable low-fouling coatings for label-free biosensing in complex biological media: advances and applications. 3927-3953 (2015). doi:10.1007/s00216-015-8606-5
[28] Wang, A. et al. Isolation and identification of *Sclerotinia* stem rot causal pathogen in *Arabidopsis thaliana*. J Zhejiang Univ Sci B 9, 818-822 (2008).

What is claimed is:

1. A biosensor for detecting the presence of and/or the amount of at least one fungal plant pathogen in a sample, comprising:
   a support structure;
   at least two interdigitated electrodes coupled to the support structure, wherein at least one of the at least two interdigitated electrodes is functionalized with a linker comprising a boronic acid functional group coupled to at least one antibody or fragment thereof that recognizes the at least one fungal plant pathogen; and
   an impedance measurement circuit coupled to the at least two interdigitated electrodes,
   wherein the at least one antibody or fragment thereof specifically binds at least *Sclerotinia sclerotiorum*.

2. The biosensor of claim 1, wherein the linker is a SAM, a macromolecule, or a thin layer of polymer.

3. The biosensor of claim 2, wherein the linker is a SAM that comprises a thiol head group.

4. The biosensor of claim 1, wherein fingers of a pair of interdigitated electrodes, arranged together in an array, have an about square shape.

5. The biosensor of claim 1, wherein the biosensor is a non-faradaic biosensor.

6. The biosensor of claim 1, wherein the at least one antibody or fragment thereof specifically binds a spore of *Sclerotinia sclerotiorum* or at least one airborne ascospore or conidiospore released from the *Sclerotinia sclerotiorum*.

7. A biosensor for detecting the presence of and/or the amount of at least one fungal plant pathogen in a sample, comprising:
   a support structure;
   at least two interdigitated electrodes coupled to the support structure, wherein at least one of the at least two interdigitated electrodes is functionalized with a linker comprising a boronic acid functional group coupled to at least one antibody or fragment thereof that recognizes the at least one fungal plant pathogen; and
   an impedance measurement circuit coupled to the at least two interdigitated electrodes,
   wherein the at least one antibody or fragment thereof specifically binds an ascospore or conidiospore of *Sclerotinia sclerotiorum*.

* * * * *